(12) United States Patent
McClure et al.

(10) Patent No.: US 9,764,134 B2
(45) Date of Patent: Sep. 19, 2017

(54) VISUAL PROSTHESIS

(75) Inventors: Kelly H. McClure, Simi Valley, CA (US); Arup Roy, Santa Clarita, CA (US); Sumit Yadav, Los Angeles, CA (US); Richard Agustin Castro, Pasadena, CA (US); Susan McCord, Santa Monica, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 1234 days.

(21) Appl. No.: 11/881,433

(22) Filed: Jul. 27, 2007

(65) Prior Publication Data

US 2008/0027510 A1 Jan. 31, 2008

Related U.S. Application Data

(60) Provisional application No. 60/833,866, filed on Jul. 28, 2006, provisional application No. 60/838,312, filed on Aug. 16, 2006, provisional application No. 60/848,458, filed on Sep. 29, 2006.

(51) Int. Cl.
*A61N 1/36* (2006.01)
*A61N 1/378* (2006.01)
*A61N 1/05* (2006.01)

(52) U.S. Cl.
CPC ....... *A61N 1/36046* (2013.01); *A61N 1/3787* (2013.01); *A61N 1/0543* (2013.01)

(58) Field of Classification Search
CPC ............ A61N 1/36046; A61N 1/36032; A61N 1/0541; A61N 1/0543; A61F 11/04; A61F 9/08

USPC ...................................... 607/53–54, 57, 137
See application file for complete search history.

(56) References Cited

U.S. PATENT DOCUMENTS

| | | | |
|---|---|---|---|
| 3,782,364 A * | 1/1974 | Watt | 600/558 |
| 4,979,508 A | 12/1990 | Beck | |
| 5,109,844 A | 5/1992 | de Juan, Jr. et al. | |
| 5,159,927 A * | 11/1992 | Schmid | 607/53 |
| 5,935,155 A * | 8/1999 | Humayun et al. | 607/54 |
| 5,944,747 A | 8/1999 | Greenberg et al. | |
| 6,074,775 A * | 6/2000 | Gartstein et al. | 429/53 |
| 6,157,861 A * | 12/2000 | Faltys et al. | 607/57 |
| 6,400,989 B1 | 6/2002 | Eckmiller | |
| 6,458,157 B1 | 10/2002 | Suaning | |
| 6,718,209 B2 | 4/2004 | Williamson et al. | |
| 6,780,182 B2 * | 8/2004 | Bowman et al. | 606/41 |
| 6,974,533 B2 | 12/2005 | Zhou | |
| 7,027,874 B1 * | 4/2006 | Sawan et al. | 607/116 |

(Continued)

FOREIGN PATENT DOCUMENTS

DE 103 15 397 A1 10/2004

*Primary Examiner* — Christopher D Koharski
*Assistant Examiner* — Roland Dinga
(74) *Attorney, Agent, or Firm* — Scott Dunbar

(57) ABSTRACT

A visual prosthesis apparatus and a method for providing artificial vision are disclosed in the present disclosure. The visual prosthesis apparatus comprises a camera for capturing a video image, a video processing unit configured to convert the video image to stimulation patterns, and a retinal stimulation system configured stimulate neural tissue in a subjects eye based on the stimulation patterns. An artificial vision may be provided by capturing a video image, converting the video image to stimulation patterns, and stimulating neural tissue in a subjects eye based on the stimulation patterns.

34 Claims, 13 Drawing Sheets

(56) References Cited

U.S. PATENT DOCUMENTS

| | | | |
|---|---|---|---|
| 7,818,061 B1* | 10/2010 | Palmer | 607/32 |
| 2002/0010496 A1* | 1/2002 | Greenberg et al. | 607/54 |
| 2002/0038134 A1* | 3/2002 | Greenberg | A61N 1/0543 |
| | | | 607/1 |
| 2002/0091421 A1 | 7/2002 | Greenberg et al. | |
| 2002/0095193 A1 | 7/2002 | Ok et al. | |
| 2003/0144711 A1* | 7/2003 | Pless et al. | 607/60 |
| 2004/0127957 A1* | 7/2004 | Fujikado et al. | 607/54 |
| 2004/0230247 A1* | 11/2004 | Stein et al. | 607/32 |
| 2004/0236389 A1* | 11/2004 | Fink et al. | 607/54 |
| 2005/0222624 A1 | 10/2005 | Greenberg et al. | |
| 2005/0245991 A1* | 11/2005 | Faltys | H04R 25/70 |
| | | | 607/57 |
| 2006/0106432 A1* | 5/2006 | Sawan et al. | 607/54 |
| 2006/0129207 A1* | 6/2006 | Fried et al. | 607/54 |
| 2008/0061961 A1* | 3/2008 | John | 340/539.12 |
| 2009/0018419 A1* | 1/2009 | Torch | 600/318 |
| 2009/0312817 A1* | 12/2009 | Hogle et al. | 607/54 |

\* cited by examiner

VISUAL PROSTHESIS

CROSS REFERENCE TO RELATED APPLICATIONS

This application claims the benefit of U.S. provisional Patent Application Ser. No. 60/833,866, filed Jul. 28, 2006 for "Visual Prosthesis" by Robert J. Greenberg and Kelly H. McClure, U.S. provisional Patent Application Ser. No. 60/838,312, filed Aug. 16, 2006 for "Visual Prosthesis" by Robert J. Greenberg and Kelly H. McClure, U.S. provisional Patent Application Ser. No. 60/848,458, filed Sep. 29, 2006 for "Chapter 2: Product Description" by Robert J. Greenberg, Kelly H. McClure, and Neil Hamilton Talbot, the disclosure of all of which is incorporated herein by reference.

FEDERALLY SPONSORED RESEARCH OR DEVELOPMENT

The present invention was made with support from the United States Government under Grant number R24EY12893-01, awarded by the National Institutes of Health. The United States Government has certain rights in the invention.

FIELD

The present disclosure relates to visual prostheses configured to provide neutral stimulation for the creation of artificial vision.

BACKGROUND

In 1755 LeRoy passed the discharge of a Leyden jar through the orbit of a man who was blind from cataract and the patient saw "flames passing rapidly downwards." Ever since, there has been a fascination with electrically elicited visual perception. The general concept of electrical stimulation of retinal cells to produce these flashes of light or phosphenes has been known for quite some time. Based on these general principles, some early attempts at devising a prosthesis for aiding the visually impaired have included attaching electrodes to the head or eyelids of patients. While some of these early attempts met with some limited success, these early prosthetic devices were large, bulky and could not produce adequate simulated vision to truly aid the visually impaired.

In the early 1930's, Foerster investigated the effect of electrically stimulating the exposed occipital pole of one cerebral hemisphere. He found that, when a point at the extreme occipital pole was stimulated, the patient perceived a small spot of light directly in front and motionless (a phosphene). Subsequently, Brindley and Lewin (1968) thoroughly studied electrical stimulation of the human occipital (visual) cortex. By varying the stimulation parameters, these investigators described in detail the location of the phosphenes produced relative to the specific region of the occipital cortex stimulated. These experiments demonstrated: (1) the consistent shape and position of phosphenes; (2) that increased stimulation pulse duration made phosphenes brighter; and (3) that there was no detectable interaction between neighboring electrodes which were as close as 2.4 mm apart.

As intraocular surgical techniques have advanced, it has become possible to apply stimulation on small groups and even on individual retinal cells to generate focused phosphenes through devices implanted within the eye itself. This has sparked renewed interest in developing methods and apparatuses to aid the visually impaired. Specifically, great effort has been expended in the area of intraocular visual prosthesis devices in an effort to restore vision in cases where blindness is caused by photoreceptor degenerative retinal diseases such as retinitis pigmentosa and age related macular degeneration which affect millions of people worldwide.

Neural tissue can be artificially stimulated and activated by prosthetic devices that pass pulses of electrical current through electrodes on such a device. The passage of current causes changes in electrical potentials across visual neuronal membranes, which can initiate visual neuron action potentials, which are the means of information transfer in the nervous system.

Based on this mechanism, it is possible to input information into the nervous system by coding the information as a sequence of electrical pulses which are relayed to the nervous system via the prosthetic device. In this way, it is possible to provide artificial sensations including vision.

One typical application of neural tissue stimulation is in the rehabilitation of the blind. Some forms of blindness involve selective loss of the light sensitive transducers of the retina. Other retinal neurons remain viable, however, and may be activated in the manner described above by placement of a prosthetic electrode device on the inner (toward the vitreous) retinal surface (epiretial). This placement must be mechanically stable, minimize the distance between the device electrodes and the visual neurons, and avoid undue compression of the visual neurons.

In 1986, Bullara (U.S. Pat. No. 4,573,481) patented an electrode assembly for surgical implantation on a nerve. The matrix was silicone with embedded iridium electrodes. The assembly fit around a nerve to stimulate it.

Dawson and Radtke stimulated cat's retina by direct electrical stimulation of the retinal ganglion cell layer. These experimenters placed nine and then fourteen electrodes upon the inner retinal layer (i.e., primarily the ganglion cell layer) of two cats. Their experiments suggested that electrical stimulation of the retina with 30 to 100 uA current resulted in visual cortical responses. These experiments were carried out with needle-shaped electrodes that penetrated the surface of the retina (see also U.S. Pat. No. 4,628,933 to Michelson).

The Michelson '933 apparatus includes an array of photosensitive devices on its surface that are connected to a plurality of electrodes positioned on the opposite surface of the device to stimulate the retina. These electrodes are disposed to form an array similar to a "bed of nails" having conductors which impinge directly on the retina to stimulate the retinal cells. U.S. Pat. No. 4,837,049 to Byers describes spike electrodes for neural stimulation. Each spike electrode pierces neural tissue for better electrical contact. U.S. Pat. No. 5,215,088 to Norman describes an array of spike electrodes for cortical stimulation. Each spike pierces cortical tissue for better electrical contact.

The art of implanting an intraocular prosthetic device to electrically stimulate the retina was advanced with the introduction of retinal tacks in retinal surgery. De Juan, et al. at Duke University Eye Center inserted retinal tacks into retinas in an effort to reattach retinas that had detached from the underlying choroid, which is the source of blood supply for the outer retina and thus the photoreceptors. See, e.g., E. de Juan, et al., 99 Am. J. Ophthalmol. 272 (1985). These retinal tacks have proved to be biocompatible and remain embedded in the retina, and choroid/sclera, effectively pinning the retina against the choroid and the posterior aspects of the globe. Retinal tacks are one way to attach a retinal array to the retina. U.S. Pat. No. 5,109,844 to de Juan describes a flat electrode array placed against the retina for visual stimulation. U.S. Pat. No. 5,935,155 to Humayun describes a visual prosthesis for use with the flat retinal array described in de Juan.

SUMMARY

According to a first aspect, a visual prosthesis apparatus is disclosed, the a visual prosthesis apparatus comprising: a camera for capturing a video image; a video processing unit associated with the camera, the video processing unit configured to convert the video image to stimulation patterns and comprising at least one indicator light to provide visual indication of operating status of the apparatus; and a retinal stimulation system configured to stimulate neural tissue in a subject's eye based on the stimulation patterns.

According to a second aspect, a visual prosthesis apparatus is disclosed, the a visual prosthesis apparatus comprising: a camera for capturing a video image; a video processing unit associated with the camera, the video processing unit configured to convert the video image to stimulation patterns and comprising a speaker to provide audible alerts to indicate various operational conditions of the apparatus; and a retinal stimulation system configured to stimulate neural tissue in a subject's eye based on the stimulation patterns.

According to a third aspect, a video processing unit configured to convert a video image to stimulation patterns for stimulating neural tissue in a subject's eye and comprising at least one indicator light to provide visual indication of an operating status of at least the video processing unit.

According to a fourth aspect, a video processing unit configured to convert a video image to stimulation patterns for stimulating neural tissue in a subject's eye and comprises a speaker to provide audible alerts to indicate various operational conditions of at least the video processing unit.

According to a fifth aspect, a method for providing artificial vision is disclosed, the method comprising: capturing a video image; converting the video image to stimulation patterns; providing a visual indication of operating status of a system; and stimulating neural tissue in a subject's eye based on the stimulation patterns.

According to a sixth aspect, a method for providing artificial vision is disclosed, the method comprising: capturing a video image; converting the video image to stimulation patterns; providing an audio indication of operating status of a system; and stimulating neural tissue in a subject's eye based on the stimulation patterns.

Further embodiments are shown in the specification, drawings and claims of the present application.

BRIEF DESCRIPTION OF THE FIGURES

FIGS. 13-1, 13-2, 13-3 and 13-4 show an exemplary embodiment of a video processing unit. FIG. 13-1 should be viewed at the left of FIG. 13-2. FIG. 13-3 should be viewed at the left of FIG. 13-4. FIGS. 13-1 and 13-2 should be viewed on top of FIGS. 13-3 and 13-4.

In the following description, like reference numbers are used to identify like elements. Furthermore, the drawings are intended to illustrate major features of exemplary embodiments in a diagrammatic manner. The drawings are not intended to depict every feature of every implementation nor relative dimensions of the depicted elements, and are not drawn to scale.

DETAILED DESCRIPTION

The present disclosure is concerned with a visual apparatus and a method for creation of artificial vision. In particular, the present disclosure provides an interface and method for controlling a visual prosthesis (i.e. device) implanted in an individual patient (i.e. subject) to create artificial vision.

Figure 1:
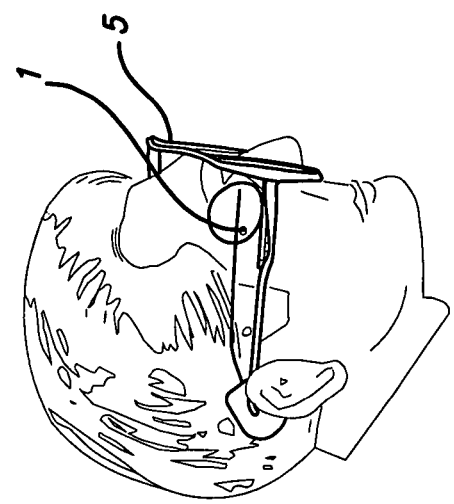
FIG. 1 shows a visual prosthesis apparatus according to the present disclosure.

FIG. 1 shows a visual prosthesis apparatus. The visual apparatus comprises, in combination, an implantable retinal stimulation system 1 and a video capture/transmission apparatus or visor embodied in visor/Glasses 5. An exemplary retinal stimulation system 1 is shown in more detail in FIGS. 2 and 3 and an exemplary visor 5 are shown in more detail in FIGS. 6 and 7.

The retinal stimulation system 1 is further disclosed in U.S. application Ser. No. 11/207,644, filed Aug. 19, 2005 for "Flexible Circuit Electrode Array" by Robert J. Greenberg, et, al. incorporated herein by reference, and is intended for use in subjects with retinitis pigmentosa. The visor 5 is further disclosed in International Patent Application No. PCT/US07/13918, filed on Jun. 14, 2007 and entitled "APPARATUS AND METHOD FOR ELECTRICAL STIMULATION OF HUMAN RETINA," also incorporated herein by reference.

Figure 2:
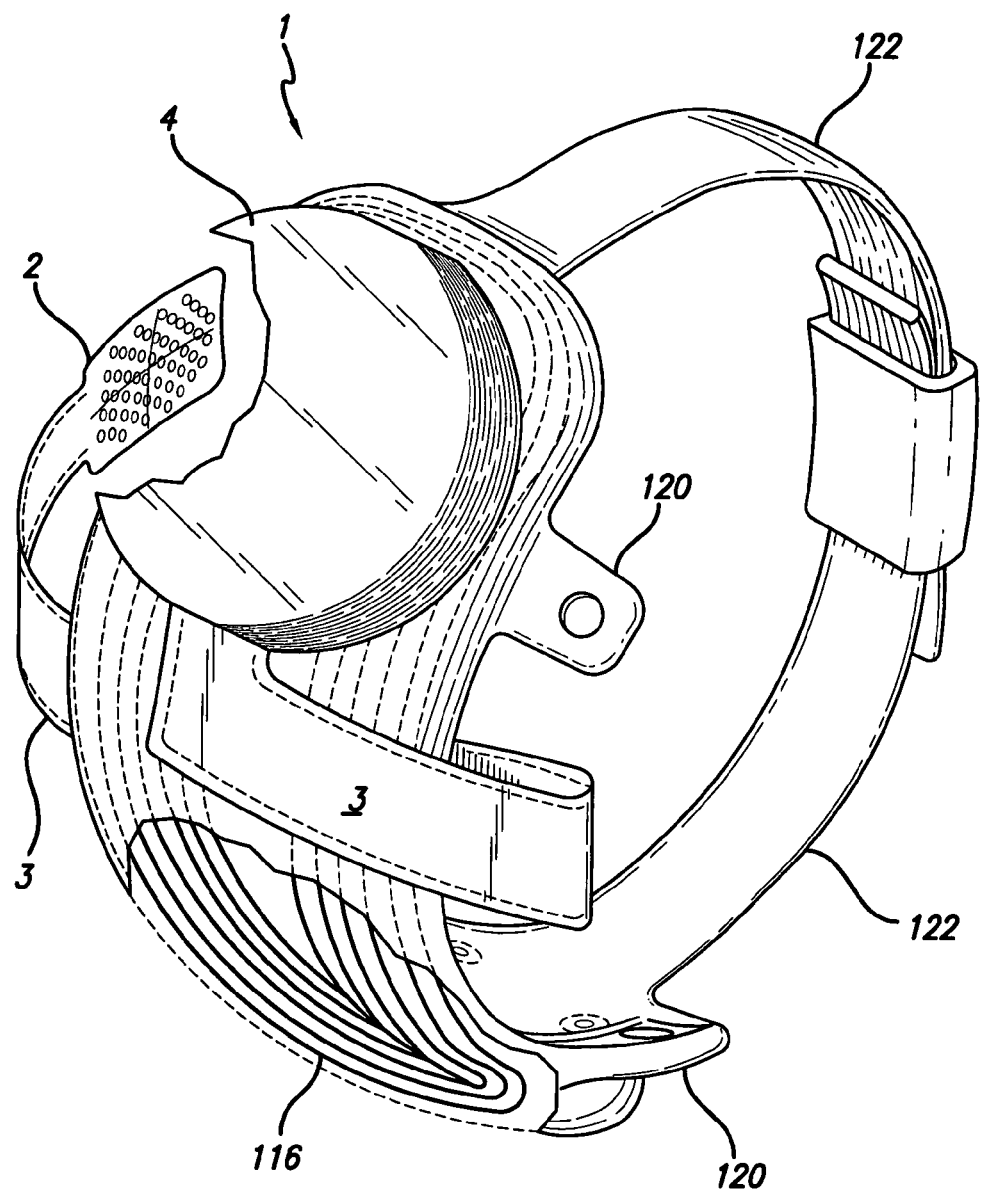
FIGS. 2 and 3 show a retinal stimulation system adapted to be implanted into a subject.
Figure 3:
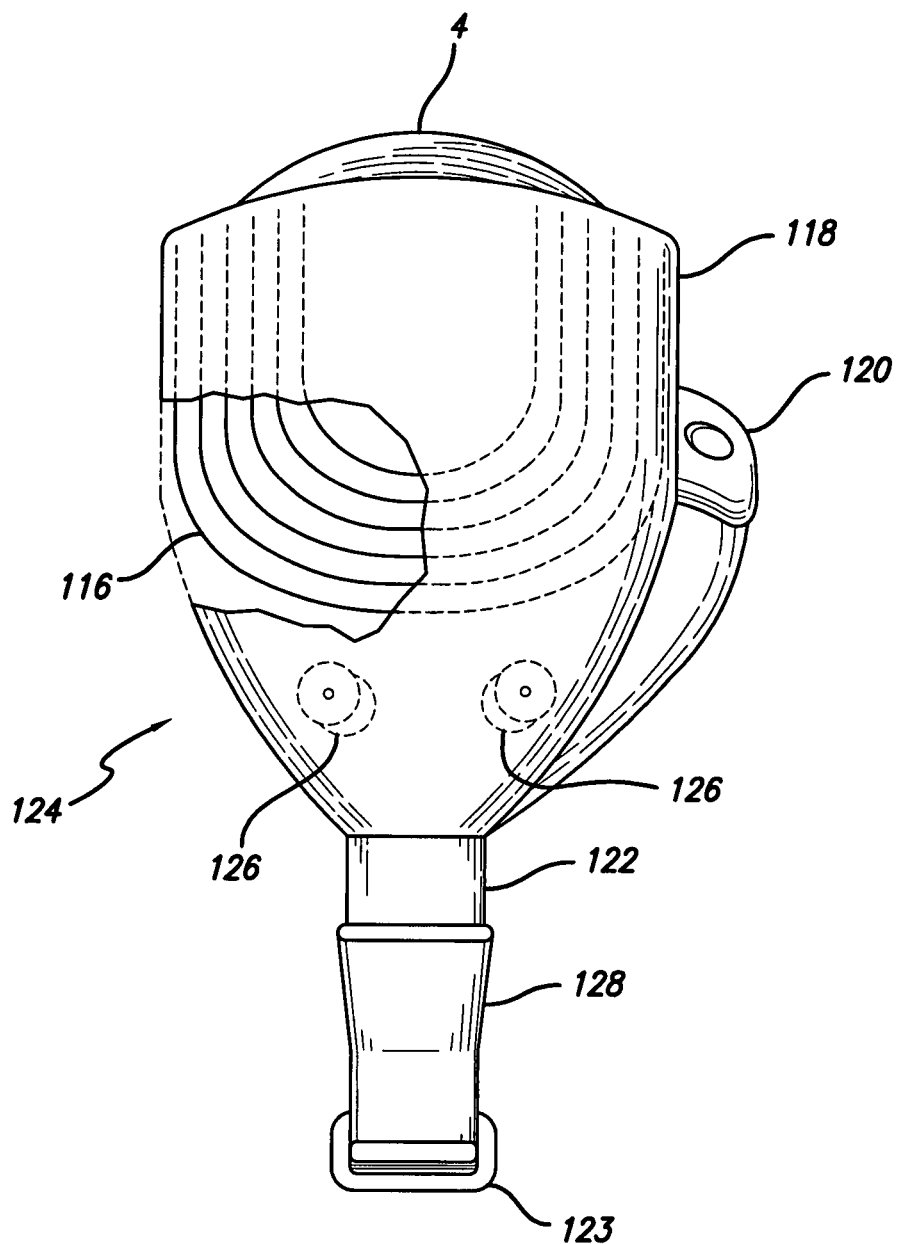

The exemplary retinal stimulation system 1, shown in FIGS. 2 and 3, is an implantable electronic device containing an inductive coil 116 and an electrode array 2 that is electrically coupled by a cable 3 that pierces sclera of the subject's eye to an electronics package 4, external to the sclera. The retinal stimulation system 1 is designed, for example, to elicit visual percepts in blind subjects with retinitis pigmentosa.

Human vision provides a field of view that is wider than it is high. This is partially due to fact that we have two eyes, but even a single eye provides a field of view that is approximately 90° high and 140° to 160° degrees wide. It is therefore, advantageous to provide a flexible circuit electrode array 2 that is wider than it is tall. This is equally applicable to a cortical visual array. In which case, the wider dimension is not horizontal on the visual cortex, but corresponds to horizontal in the visual scene.

Figure 8:
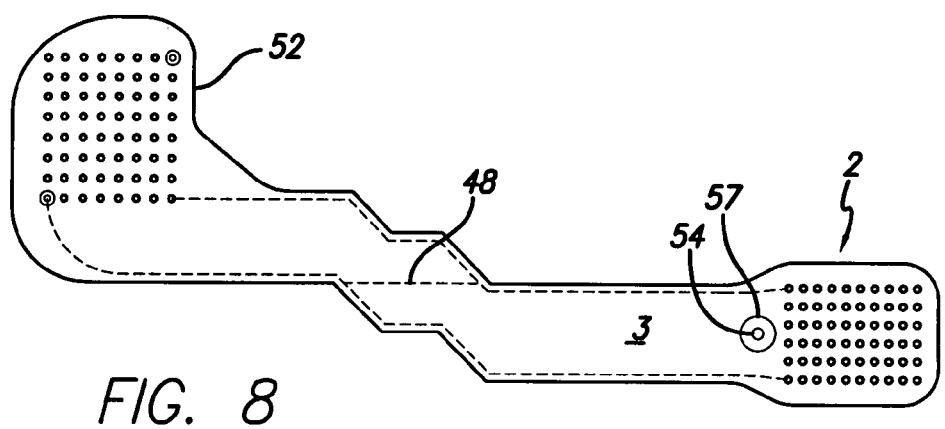
FIG. 8 shows a flexible circuit electrode array, also shown in FIG. 2.

FIG. 8 shows the flexible circuit electrode array 2 prior to folding and attaching to the electronics package 4 of FIG. 2.

At one end of the flexible circuit cable 3 is an interconnection pad 52 for connection to the electronics package 4. At the other end of the flexible circuit cable 3 is the flexible circuit electrode array 2. Further, an attachment point 54 may be provided near the flexible circuit electrode array 2. A retina tack (not shown) is placed through the attachment point 54 to hold the flexible circuit electrode array 2 to the retina. A stress relief 57 may be provided surrounding the attachment point 54. The stress relief 57 may be made of a softer polymer than the flexible circuit, or it may include cutouts or thinning of the polymer to reduce the stress transmitted from the retina tack to the flexible circuit electrode array 2. The flexible circuit cable 3 may be formed in a dog leg pattern so than when it is folded at fold 48 it effectively forms a straight flexible circuit cable 3 with a narrower portion at the fold 48 for passing through the sclerotomy. The electrode array 2 may comprise a polyimide cable that houses wire conductors and an array of exposed platinum electrodes in a grid. In one embodiment, there are sixty electrodes arranged in a 6×10 grid.

The electronics package 4 of FIGS. 2 and 3 can be electrically coupled to the inductive coil 116. In one aspect, the inductive coil 116 contains a receiver and transmitter antennae made from wound wire. Alternatively, the inductive coil 116 may be made from a thin film polymer sandwich with wire traces deposited between layers of thin film polymer. The electronics package 4 may contain components and an Application Specific Integrated Circuit (ASIC) for processing the received data and using the received power to generate the required stimulation output. The electronics package 4 and the inductive coil 116 may be held together by a molded body 118 shown in FIG. 3. As also shown in FIG. 3, the molded body 118 may also include suture tabs 120 shown in FIG. 3. The molded body narrows to form a strap 122 which surrounds the sclera and holds the molded body 118, inductive coil 116, and electronics package 4 in place. The molded body 118, suture tabs 120 and strap 122 are preferably an integrated unit made of silicone elastomer. Silicone elastomer can be formed in a pre-curved shape to match the curvature of a typical sclera. Furthermore, silicone remains flexible enough to accommodate implantation and to adapt to variations in the curvature of an individual sclera. In one aspect, the inductive coil 116 and molded body 118 are oval shaped, and in this way, a strap 122 can better support the oval shaped coil.

The eye moves constantly. The eye moves to scan a scene and also has a jitter motion to prevent image stabilization. Even though such motion is useless in the blind, it often continues long after a person has lost their sight. Thus, in one embodiment of the present disclosure, the entire retinal stimulation system 1 of the prosthesis is attached to and supported by the sclera of a subject. By placing the device under the rectus muscles with the electronics package in an area of fatty tissue between the rectus muscles, eye motion does not cause any flexing which might fatigue, and eventually damage, the device.

FIG. 3 shows a side view of the retinal stimulation system 1, in particular, emphasizing the fan tail 124. When the retinal prosthesis is implanted, the strap 122 is passed under the eye muscles to surround the sclera. The inductive coil 116 and molded body 118 should also follow the strap under the lateral rectus muscle on the side of the sclera. The retinal stimulation system 1 of the visual prosthesis apparatus is very delicate. It is easy to tear the molded body 118 or break wires in the inductive coil 116. In order to allow the molded body 118 to slide smoothly under the lateral rectus muscle, the molded body is shaped in the form of a fan tail 124 on the end opposite the electronics package 4. Element 123 shows a retention sleeve, while elements 126 and 128 show holes for surgical positioning and a ramp for surgical positioning, respectively.

Figure 4:
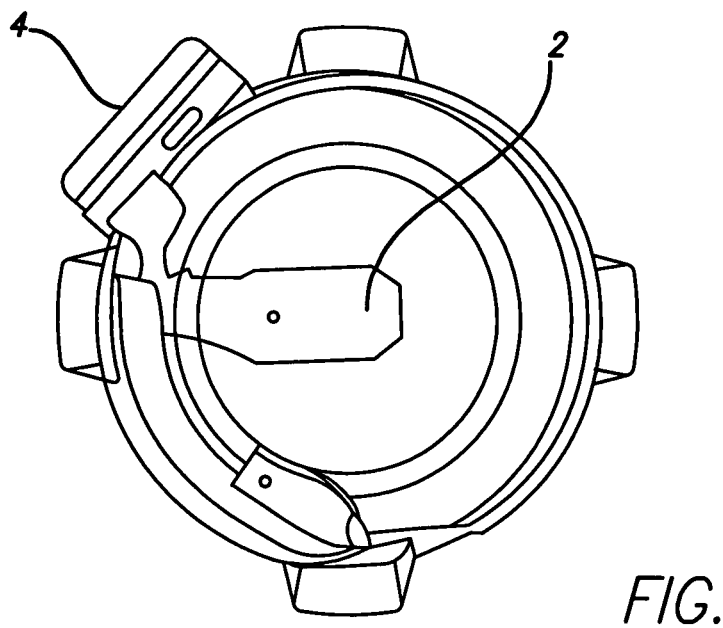
FIG. 4 shows a front view of the implanted retinal stimulation system.
Figure 5:
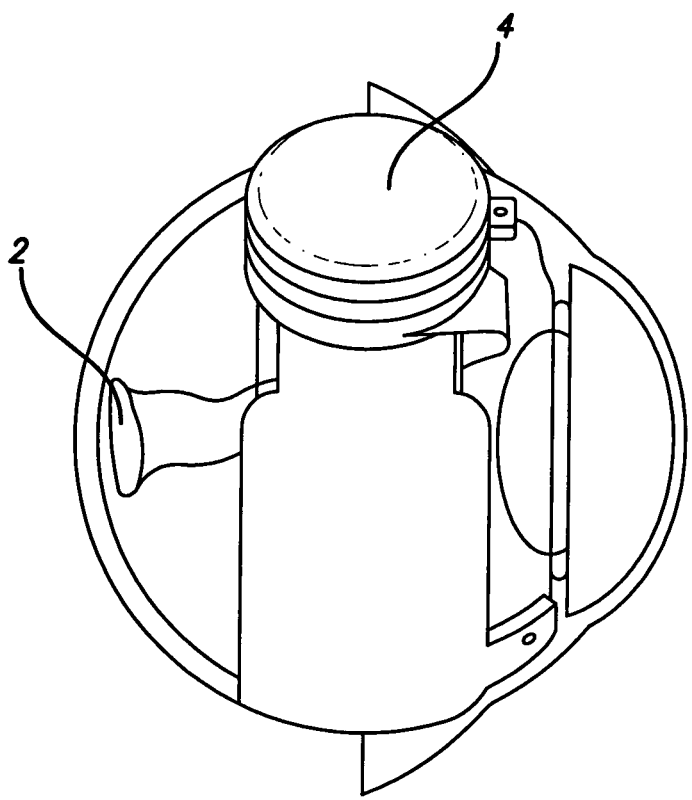
FIG. 5 shows a side view of the implanted system of FIG. 9.

FIGS. 4 and 5 show front and side views of the Retinal stimulation system 1 implanted with respect to the subject's eye 7. As shown in FIGS. 4 and 5, the electrode array 2 enters the eye through a pars plana incision and is placed on the retina over the fovea using a retinal tack. The remaining Retinal stimulation system 1 is secured to the eye by means of a scleral band held in place by a Watzke sleeve (typical of scleral procedures), and also by suture tabs. Additionally, another suture may be placed around the scleral band in the inferior medical quadrant of the eye.

Figure 6:
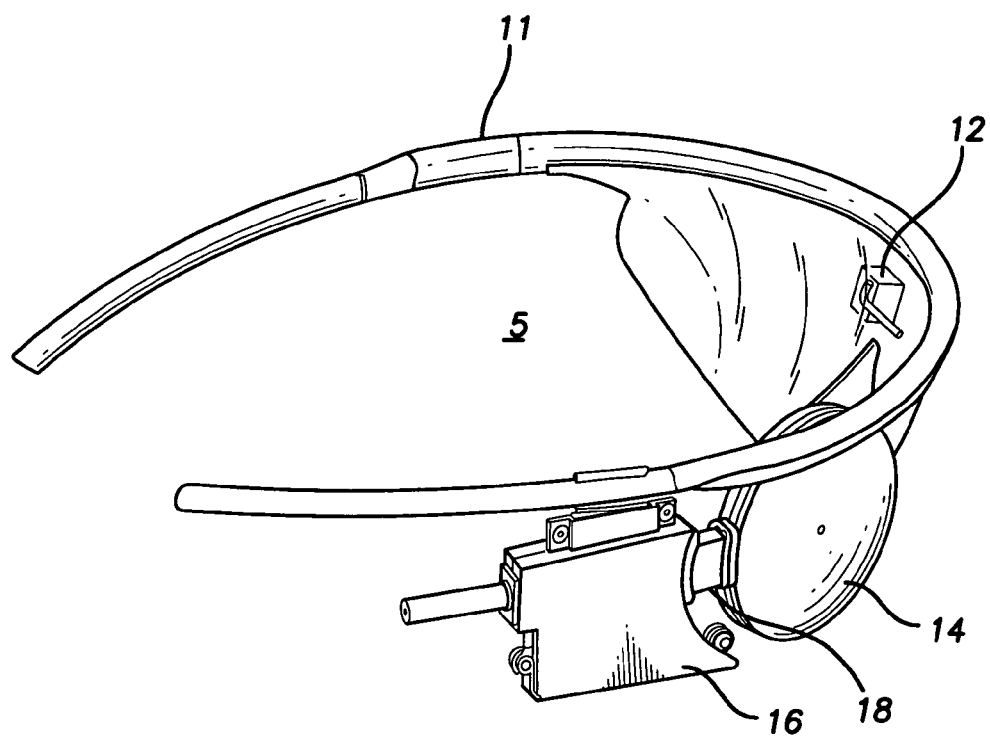
FIGS. 6 and 7 show a video capture/transmission apparatus or visor adapted to be used in combination with the retinal stimulation of FIGS. 2 and 3.
Figure 7:
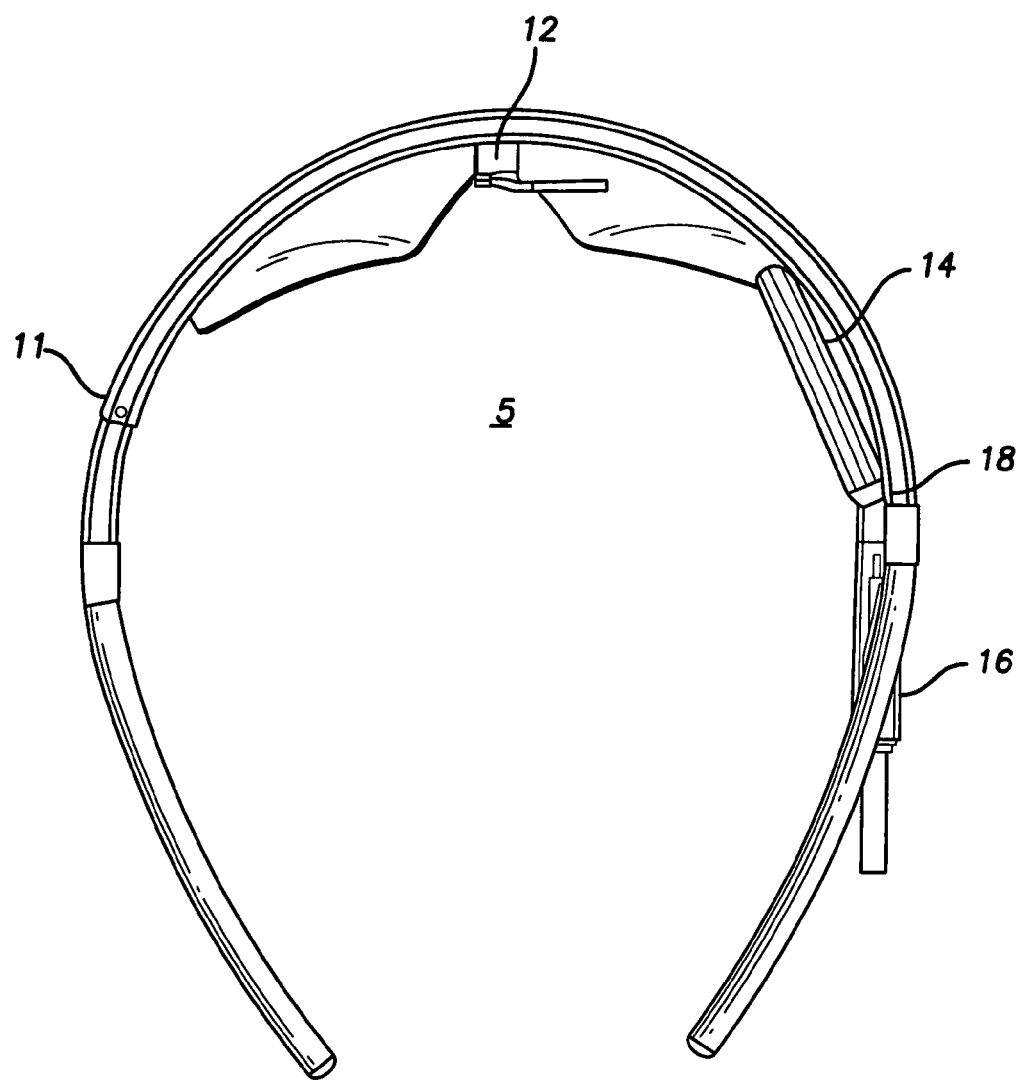

Referring to FIGS. 6 and 7, the glasses 5 may comprise, for example, a frame 11 holding a camera 12, an external coil 14 and a mounting system 16 for the external coil 14. The mounting system 16 may also enclose the RF circuitry. In this configuration, the video camera 12 captures live video. The video signal is sent to an external Video Processing Unit (VPU) 20 (shown in FIGS. 9, 11 and 12 and discussed below), which processes the video signal and subsequently transforms the processed video signal into electrical stimulation patterns or data. The electrical stimulation data are then sent to the external coil 14 that sends both data and power via radio-frequency (RF) telemetry to the coil 116 of the retinal stimulation system 1, shown in FIGS. 2 and 3. The coil 116 receives the RF commands which control the application specific integrated circuit (ASIC) which in turn delivers stimulation to the retina of the subject via a thin film electrode array (TFEA). In one aspect of an embodiment, light amplitude is recorded by the camera 12. The VPU 20 may use a logarithmic encoding scheme to convert the incoming light amplitudes into the electrical stimulation patterns or data. These electrical stimulation patterns or data may then be passed on to the Retinal Stimulation System 1, which results in the retinal cells being stimulated via the electrodes in the electrode array 2 (shown in FIGS. 2, 3 and 8). In one exemplary embodiment, the electrical stimulation patterns or data being transmitted by the external coil 14 is binary data. The external coil 14 may contain a receiver and transmitter antennae and a radio-frequency (RF) electronics card for communicating with the internal coil 116.

Figure 9:
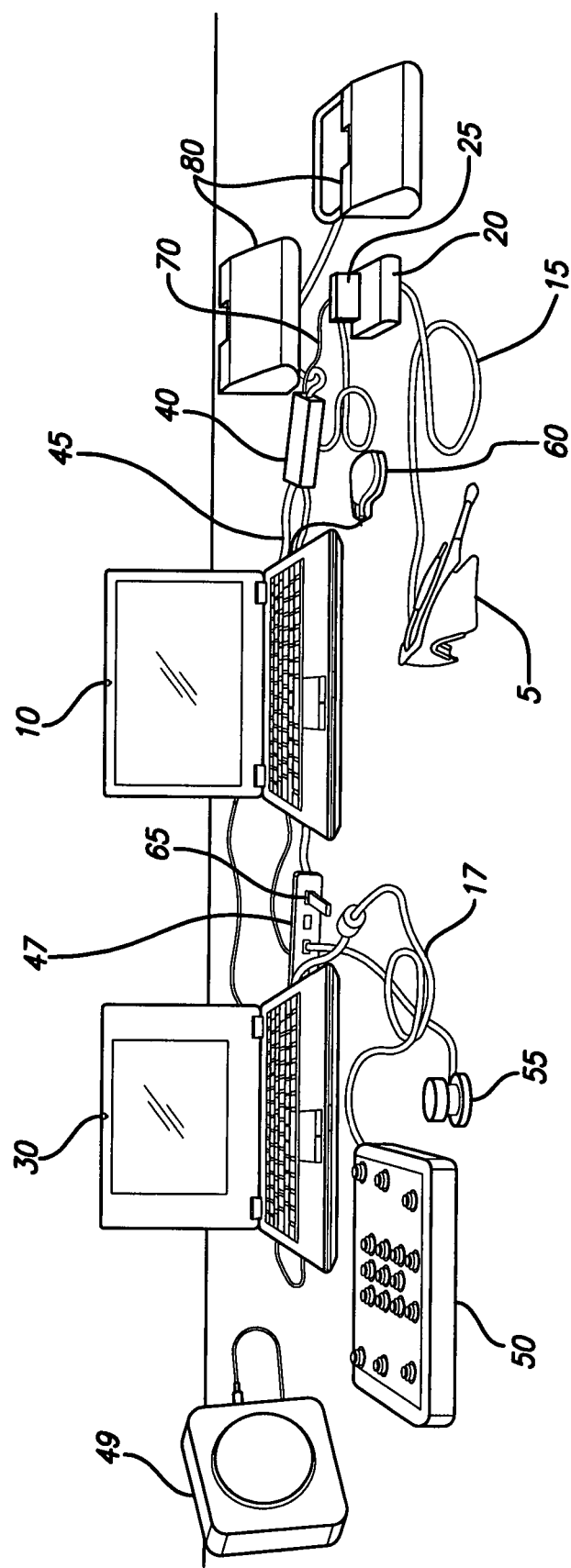
FIG. 9 shows components of a fitting system according to the present disclosure, the system also comprising the visor shown in FIGS. 4 and 5.

Referring to FIG. 9, a Fitting System (FS) may be used to configure and optimize the visual prosthesis apparatus shown in FIG. 1. The Fitting System is fully described in the related application U.S. application Ser. No. 11/796,425, filed on Apr. 27, 2007, which is incorporated herein by reference in its entirety.

The Fitting System may comprise custom software with a graphical user interface running on a dedicated laptop computer 10. Within the Fitting System are modules for performing diagnostic checks of the implant, loading and executing video configuration files, viewing electrode voltage waveforms, and aiding in conducting psychophysical experiments. A video module can be used to download a video configuration file to the Video Processing Unit (VPU) 20 discussed above and store it in non-volatile memory to control various aspects of video configuration, e.g. the spatial relationship between the video input and the electrodes. The software can also load a previously used video configuration file from the VPU 20 for adjustment.

The Fitting System can be connected to the Psychophysical Test System (PTS), located for example on a dedicated laptop 30, in order to run psychophysical experiments. In psychophysics mode, the Fitting System enables individual electrode control, permitting clinicians to construct test stimuli with control over current amplitude, pulse-width, and frequency of the stimulation. In addition, the psychophysics module allows the clinician to record subject responses. The PTS may include a collection of standard psychophysics experiments developed using for example MATLAB (MathWorks) software and other tools to allow the clinicians to develop customized psychophysics experiment scripts.

Using the psychophysics module, important perceptual parameters such as perceptual threshold, maximum comfort level, and spatial location of percepts may be reliably measured. Based on these perceptual parameters, the fitting software enables custom configuration of the transformation between video image and spatio-temporal electrode stimulation parameters in an effort to optimize the effectiveness of the retinal prosthesis for each subject.

The Fitting System laptop 10 of FIG. 9 may be connected to the VPU 20 using an optically isolated serial connection adapter 40. Because it is optically isolated, the serial connection adapter 40 assures that no electric leakage current can flow from the Fitting System laptop 10 in the even of a fault condition.

As shown in FIG. 9, the following components may be used with the Fitting System according to the present disclosure. The Video Processing Unit (VPU) 20 for the subject being tested, a Charged Battery 25 for VPU 20, the Glasses 5, a Fitting System (FS) Laptop 10, a Psychophysical Test System (PTS) Laptop 30, a PTS CD (not shown), a Communication Adapter (CA) 40, a USB Drive (Security) (not shown), a USB Drive (Transfer) 47, a USB Drive (Video Settings) (not shown), a Patient Input Device (RF Tablet) 50, a further Patient Input Device (Jog Dial) 55, Glasses Cable 15, CA-VPU Cable 70, FS-CA Cable 45, FS-PTS Cable 46, Four (4) Port USB Hub 47, Mouse 60, Test Array system 80, Archival USB Drive 49, an Isolation Transformer (not shown), adapter cables (not shown), and an External Monitor (not shown).

With continued reference to FIG. 9, the external components of the Fitting System may be configured as follows. The battery 25 is connected with the VPU 20. The PTS Laptop 30 is connected to FS Laptop 10 using the FS-PTS Cable 46. The PTS Laptop 30 and FS Laptop 10 are plugged into the Isolation Transformer (not shown) using the Adapter Cables (not shown). The Isolation Transformer is plugged into the wall outlet. The four (4) Port USB Hub 47 is connected to the FS laptop 10 at the USB port. The mouse 60 and the two Patient Input Devices 50 and 55 are connected to four (4) Port USB Hubs 47. The FS laptop 10 is connected to the Communication Adapter (CA) 40 using the FS-CA Cable 45. The CA 40 is connected to the VPU 20 using the CA-VPU Cable 70. The Glasses 5 are connected to the VPU 20 using the Glasses Cable 15.

In one exemplary embodiment, the Fitting System shown in FIG. 9 may be used to configure system stimulation parameters and video processing strategies for each subject outfitted with the visual prosthesis apparatus of FIG. 1. The fitting application, operating system, laptops 10 and 30, isolation unit and VPU 20 may be tested and configuration controlled as a system. The software provides modules for electrode control, allowing an interactive construction of test stimuli with control over amplitude, pulse width, and frequency of the stimulation waveform of each electrode in the Retinal stimulation system 1. These parameters are checked to ensure that maximum charge per phase limits, charge balance, and power limitations are met before the test stimuli are presented to the subject. Additionally, these parameters may be checked a second time by the VPU 20's firmware. The Fitting System shown in FIG. 7 may also provide a psychophysics module for administering a series of previously determined test stimuli to record subject's responses. These responses may be indicated by a keypad 50 and or verbally. The psychophysics module may also be used to reliably measure perceptual parameters such as perceptual threshold, maximum comfort level, and spatial location of percepts. These perceptual parameters may be used to custom configure the transformation between the video image and spatio-temporal electrode stimulation parameters thereby optimizing the effectiveness of the visual prosthesis for each subject. The Fitting System is fully described in the related application U.S. application Ser. No. 11/796,425, filed on Apr. 27, 2007, which is incorporated herein by reference in its entirety.

Figure 10:
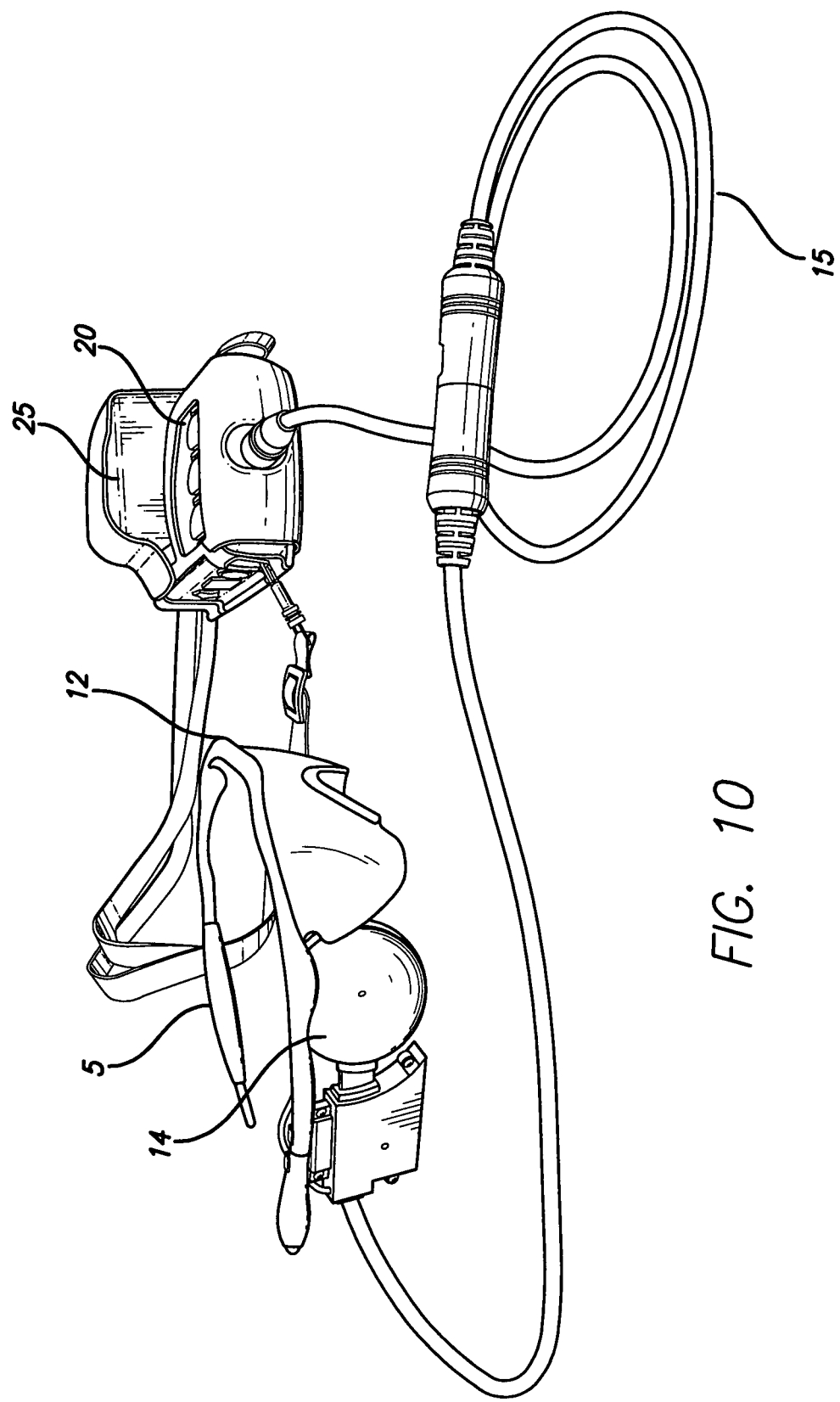
FIG. 10 shows the visual prosthesis apparatus in a stand-alone mode, i.e. comprising the visor connected to a video processing unit.

The visual prosthesis apparatus of FIG. 1 may operate in two modes: i) stand-alone mode and ii) communication mode Stand-Alone Mode Referring to FIGS. 1, 2 and 10, in the stand-alone mode, the video camera 12, on the glasses 5, captures a video image that is sent to the VPU 20. The VPU 20 processes the image from the camera 12 and transforms it into electrical stimulation patterns that are transmitted to the external coil 14. The external coil 14 sends the electrical stimulation patterns and power via radio-frequency (RF) telemetry to the implanted retinal stimulation system 1 (FIGS. 2 and 3). The internal coil 116 of the retinal stimulation system 1 receives the RF commands from the external coil 14 and transmits them to the electronics package 4 that in turn delivers stimulation to the retina via the electrode array 2. Additionally, the retinal stimulation system 1 may communicate safety and operational status back to the VPU 20 by transmitting RF telemetry from the internal coil 116 to the external coil 14. The visual prosthesis apparatus of FIG. 1 may be configured to electrically activate the retinal stimulation system 1 only when it is powered by the VPU 20 through the external coil 14. The stand-alone mode may be used for clinical testing and/or at-home use by the subject.

Communication Mode

The communication mode may be used for diagnostic testing, psychophysical testing, patient fitting and downloading of stimulation settings to the VPU 20 before transmitting data from the VPU 20 to the retinal stimulation system 1 as is done for example in the stand-alone mode described above. Referring to FIG. 9, in the communication mode, the VPU 20 is connected to the Fitting System laptop 10 using cables 70, 45 and the optically isolated serial connection adapter 40. In this mode, laptop 10 generated stimuli may be presented to the subject and programming parameters may be adjusted and downloaded to the VPU 20. The Psychophysical Test System (PTS) laptop 30 connected to the Fitting System laptop 10 may also be utilized to perform more sophisticated testing and analysis as fully described in the related application U.S. application Ser. No. 11/796,425, filed on Apr. 27, 2007, which is incorporated herein by reference in its entirety.

In one embodiment, the functionality of the retinal stimulation system 1 can also be tested pre-operatively and intra-operatively (i.e. before operation and during operation) by using an external coil 14, without the glasses 5, placed in close proximity to the retinal stimulation system 1. The coil 14 may communicate the status of the retinal stimulation system 1 to the VPU 20 that is connected to the Fitting System laptop 10 as shown in FIG. 9.

As discussed above, the VPU 20 processes the image from the camera 12 and transforms the image into electrical stimulation patterns for the retinal stimulation system 1. Filters such as edge detection filters may be applied to the electrical stimulation patterns for example by the VPU 20 to generate, for example, a stimulation pattern based on filtered video data that the VPU 20 turns into stimulation data for the retinal stimulation system 1. The images may then be reduced in resolution using a downscaling filter. In one exemplary embodiment, the resolution of the image may be reduced to match the number of electrodes in the electrode array 2 of the retinal stimulation system 1. That is, if the electrode array has, for example, sixty electrodes, the image may be reduced to a sixty channel resolution. After the reduction in resolution, the image is mapped to stimulation intensity using for example a look-up table that has been derived from testing of individual subjects. Then, the VPU 20 transmits the stimulation parameters via forward telemetry to the retinal stimulation system 1 in frames that may employ a cyclic redundancy check (CRC) error detection scheme.

Figure 11:
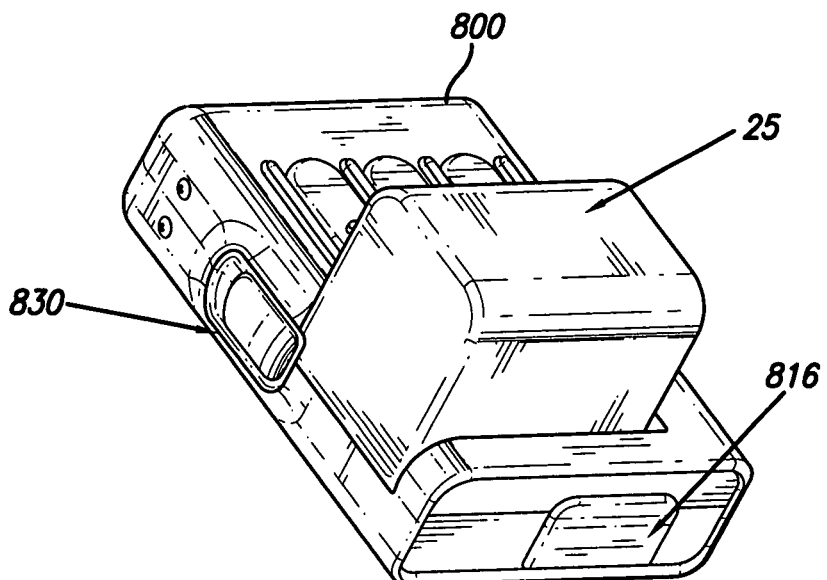
FIGS. 11-12 show the video processing unit already briefly shown with reference to FIG. 8.
Figure 12:
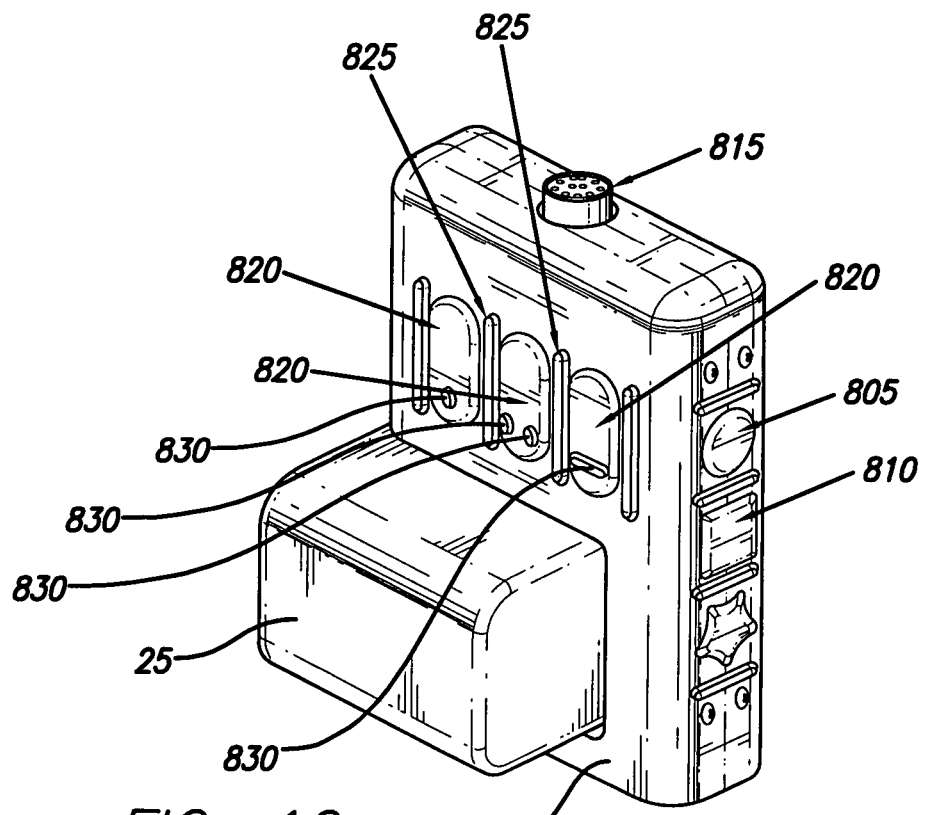
Figures 1, 13:
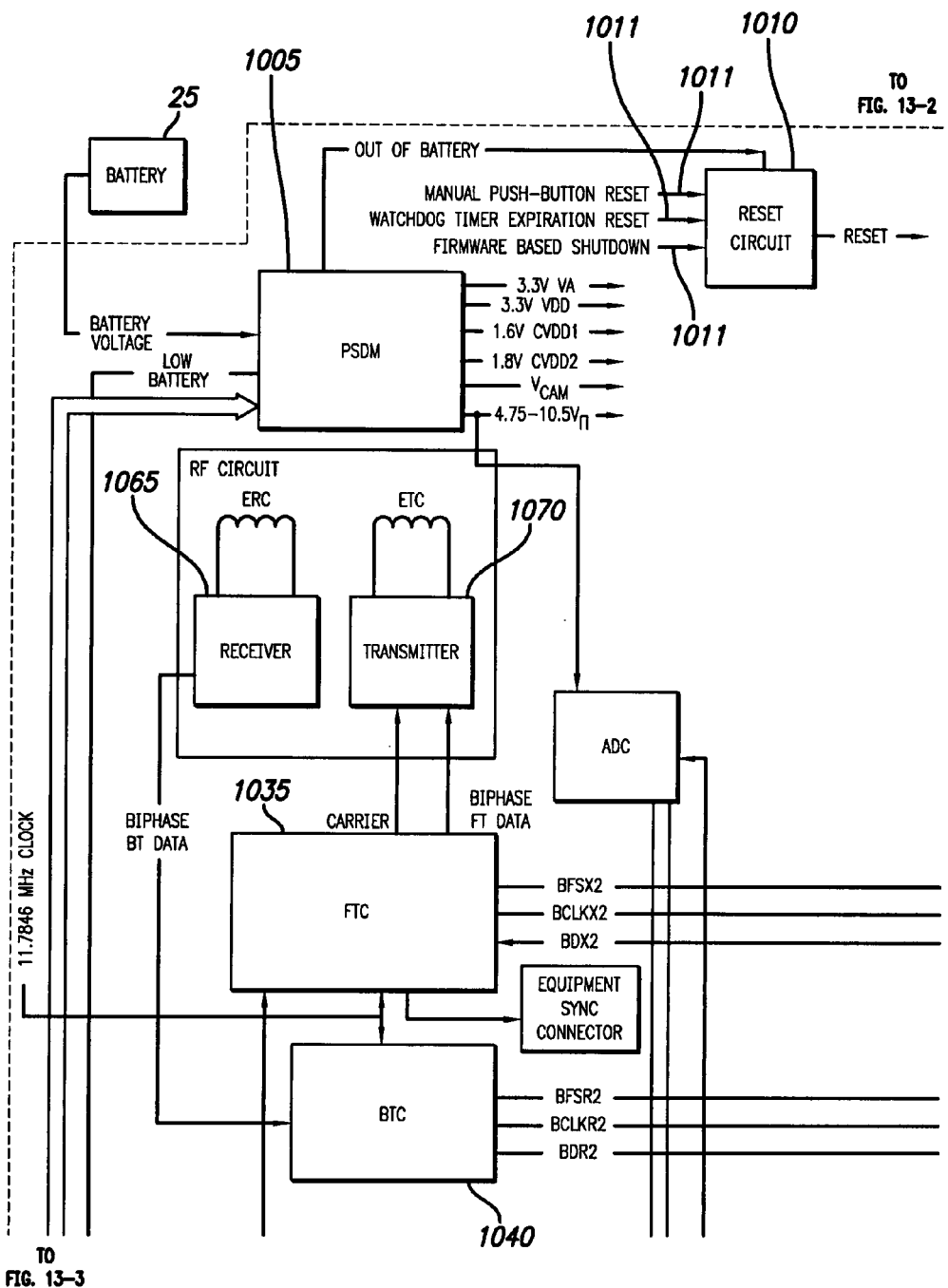
Figures 2, 13:
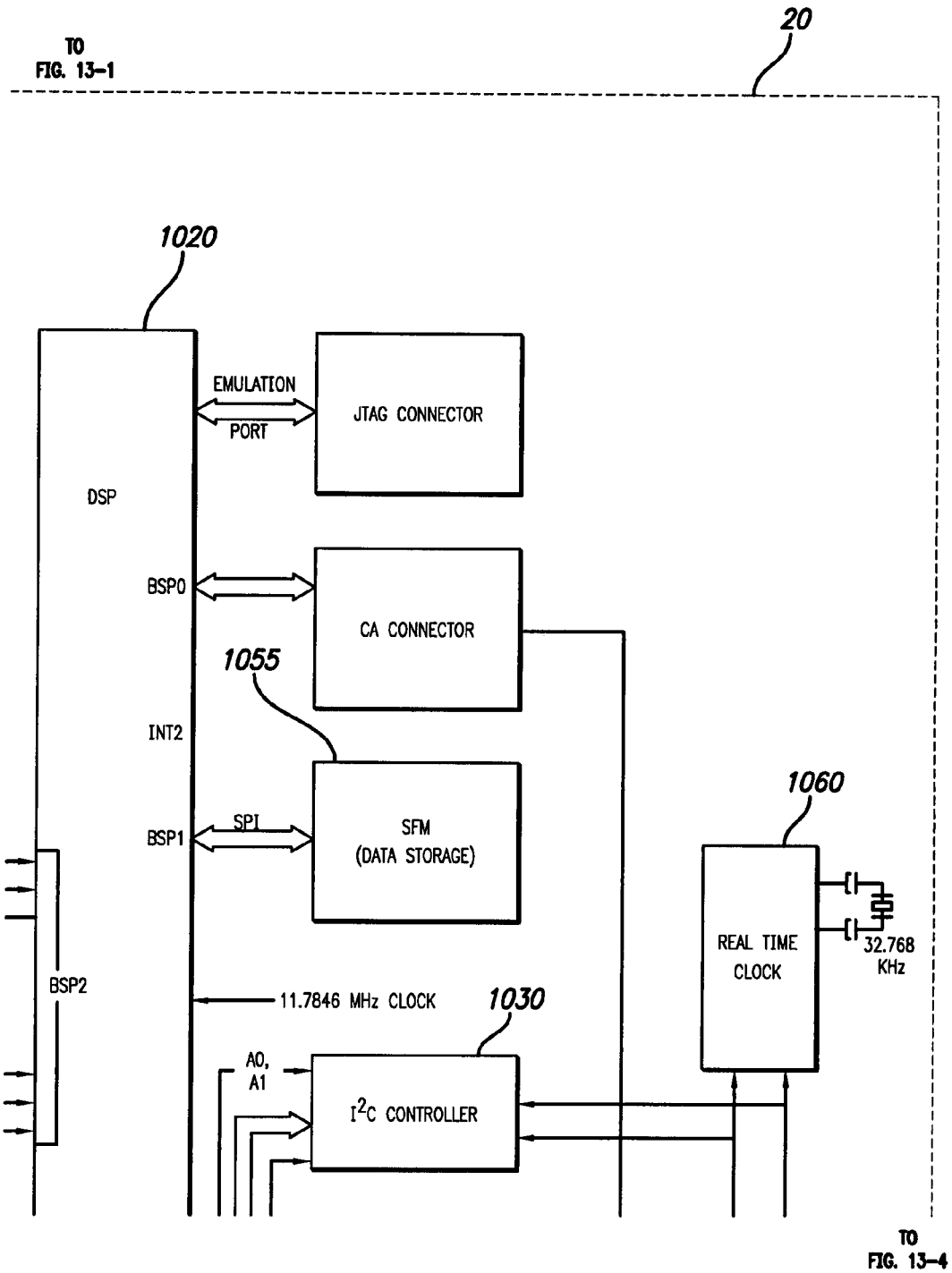
Figures 3, 13:
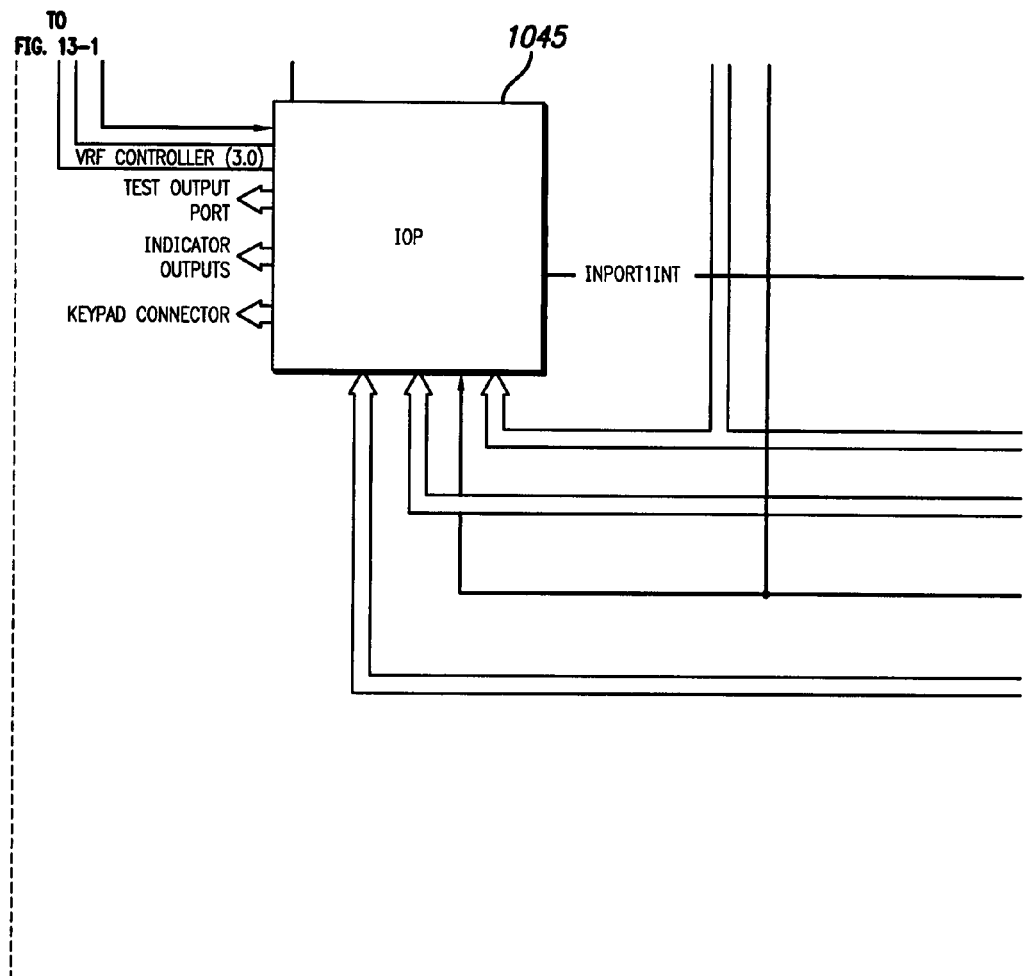
Figures 4, 13:
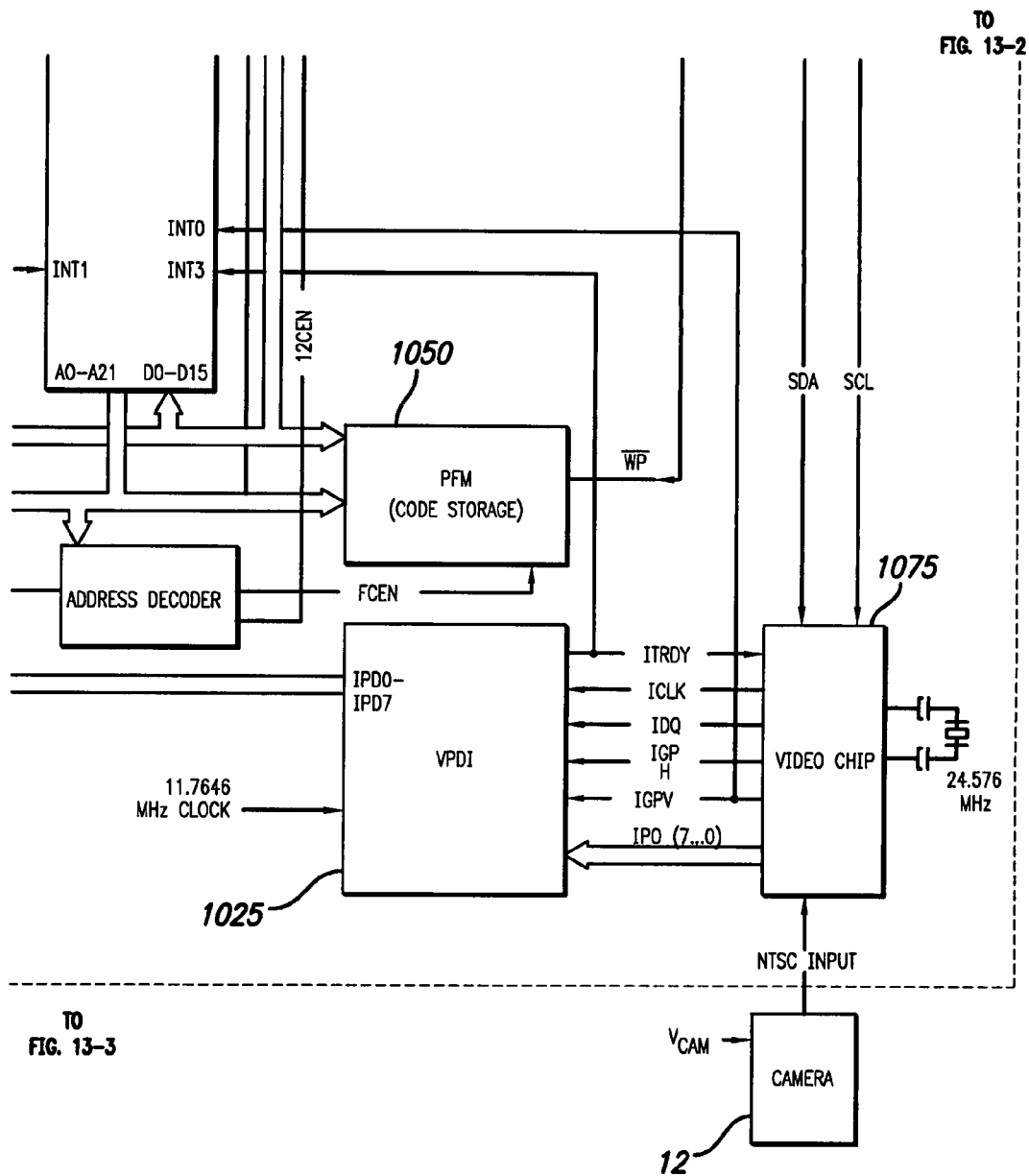

In one exemplary embodiment, the VPU 20 may be configured to allow the subject/patient i) to turn the visual prosthesis apparatus on and off, ii) to manually adjust settings, and iii) to provide power and data to the retinal stimulation system 1. Referring to FIGS. 11 and 12, the VPU 20 may comprise a case 800, power button 805 for turning the VPU 20 on and off, setting button 810, zoom buttons 820 for controlling the camera 12, connector port 815 for connecting to the Glasses 5, a connector port 816 for connecting to the laptop 10 through the connection adapter 40, indicator lights 825 to give visual indication of operating status of the system, the rechargeable battery 25 for powering the VPU 20, battery latch 830 for locking the battery 25 in the case 800, digital circuit boards (not shown), and a speaker (not shown) to provide audible alerts to indicate various operational conditions of the system. Because the VPU 20 is used and operated by a person with minimal or no vision, the buttons on the VPU 20 may be differently shaped and/or have special markings as shown in FIG. 12 to help the user identify the functionality of the button without having to look at it. As shown in FIG. 12, the power button 805 may be a circular shape while the settings button 820 may be square shape and the zoom buttons 820 may have special raised markings 830 to also identify each buttons functionality. One skilled in the art would appreciate that other shapes and markings can be used to identify the buttons without departing from the spirit and scope of the invention. For example, the markings can be recessed instead of raised.

In one embodiment, the indicator lights 825 may indicate that the VPU 20 is going through system start-up diagnostic testing when the one or more indicator lights 825 are blinking fast (more then once per second) and are green in color. The indicator lights 825 may indicate that the VPU 20 is operating normally when the one or more indicator lights 825 are blinking once per second and are green in color. The indicator lights 825 may indicate that the retinal stimulation system 1 has a problem that was detected by the VPU 20 at start-up diagnostic when the one or more indicator lights 825 are blinking for example once per five second and are green in color. The indicator lights 825 may indicate that the video signal from camera 12 is not being received by the VPU 20 when the one or more indicator lights 825 are always on and are amber color. The indicator lights 825 may indicate that there is a loss of communication between the retinal stimulation system 1 and the external coil 14 due to the movement or removal of Glasses 5 while the system is operational or if the VPU 20 detects a problem with the retinal stimulation system 1 and shuts off power to the retinal stimulation system 1 when the one or more indicator lights 825 are always on and are orange color. One skilled in the art would appreciate that other colors and blinking patterns can be used to give visual indication of operating status of the system without departing from the spirit and scope of the invention.

In one embodiment, a single short beep from the speaker (not shown) may be used to indicate that one of the buttons 825, 805 or 810 have been pressed. A single beep followed by two more beeps from the speaker (not shown) may be used to indicate that VPU 20 is turned off. Two beeps from the speaker (not shown) may be used to indicate that VPU 20 is starting up. Three beeps from the speaker (not shown) may be used to indicate that an error has occurred and the VPU 20 is about to shut down automatically. As would be clear to one skilled in the are different periodic beeping may also be used to indicate a low battery voltage warning, that there is a problem with the video signal, and/or there is a loss of communication between the retinal stimulation system 1 and the external coil 14. One skilled in the art would appreciate that other sounds can be used to give audio indication of operating status of the system without departing from the spirit and scope of the invention. For example, the beeps may be replaced by an actual prerecorded voice indicating operating status of the system.

In one exemplary embodiment, the VPU 20 is in constant communication with the retinal stimulation system 1 through forward and backward telemetry. In this document, the forward telemetry refers to transmission from VPU 20 to the retinal stimulation system 1 and the backward telemetry refers to transmissions from the Retinal stimulation system 1 to the VPU 20. During the initial setup, the VPU 20 may transmit null frames (containing no stimulation information) until the VPU 20 synchronizes with the Retinal stimulation system 1 via the back telemetry. In one embodiment, an audio alarm may be used to indicate whenever the synchronization has been lost.

In order to supply power and data to the Retinal stimulation system 1, the VPU 20 may drive the external coil 14 with a 3 MHz signal. To protect the subject, the retinal stimulation system 1 may comprise a failure detection circuit to detect direct current leakage and to notify the VPU 20 through back telemetry so that the visual prosthesis apparatus can be shut down.

One exemplary embodiment of the VPU 20 is shown in FIGS. 13-1, 13-2, 13-3 and 13-4. As shown in FIGS. 13-1, 13-2, 13-3 and 13-4, the VPU 20 may comprise: a Power Supply, a Distribution and Monitoring Circuit (PSDM) 1005, a Reset Circuit 1010, a System Main Clock (SMC) source (not shown), a Video Preprocessor Clock (VPC) source (not shown), a Digital Signal Processor (DSP) 1020, Video Preprocessor Data Interface 1025, a Video Preprocessor 1075, an I$^2$C Protocol Controller 1030, a Complex Programmable Logic device (CPLD) (not shown), a Forward Telemetry Controller (FTC) 1035, a Back Telemetry Controller (BTC) 1040, Input/Output Ports 1045, Memory Devices like a Parallel Flash Memory (PFM) 1050 and a Serial Flash Memory (SFM) 1055, a Real Time Clock 1060, an RF Voltage and Current Monitoring Circuit (VIMC) (not shown), a speaker and/or a buzzer, an RF receiver 1065, and an RF transmitter 1070.

The Power Supply, Distribution and Monitoring Circuit (PSDM) 1005 may regulate a variable battery voltage to several stable voltages that apply to components of the VPU 20. The Power Supply, Distribution and Monitoring Circuit (PSDM) 1005 may also provide low battery monitoring and depleted battery system cutoff. The Reset Circuit 1010 may have reset inputs 1011 that are able to invoke system level rest. For example, the reset inputs 1011 may be from a manual push-button reset, a watchdog timer expiration, and/or firmware based shutdown. The System Main Clock (SMC) source is a clock source for DSP 1020 and CPLD. The Video Preprocessor Clock (VPC) source is a clock source for the Video Processor. The DSP 1020 may act as the central processing unit of the VPU 20. The DSP 1020 may communicate with the rest of the components of the VPU 20 through parallel and serial interfaces. The Video Processor 1075 may convert the NTSC signal from the camera 12 into a down-scaled resolution digital image format. The Video Processor 1075 may comprise a video decoder (not shown) for converting the NTSC signal into high-resolution digitized image and a video scaler (not shown) for scaling down the high-resolution digitized image from the video decoder to an intermediate digitized image resolution. The video decoder may be composed of an Analog Input Processing, Chrominance and Luminance Processing and Brightness Contrast and Saturation (BSC) Control circuits. The video scaler may be composed of Acquisition control, Pre-scaler, BSC-control, Line Buffer and Output Interface. The I²C Protocol Controller 1030 may serve as a link between the DSP 1020 and the I²C bus. The I²C Protocol Controller 1030 may be able to convert the parallel bus interface of the DSP 1020 to the I²C protocol bus or vise versa. The I²C Protocol Controller 1030 may also be connected to the Video Processor 1075 and the Real Time Clock 1060. The VPDI 1025 may contain a tri-state machine to shift video data from Video Preprocessor 1075 to the DSP 1020. The Forward Telemetry Controller (FTC) 1035 packs 1024 bits of forward telemetry data into a forward telemetry frame. The FTC 1035 retrieves the forward telemetry data from the DSP 1020 and converts the data from logic level to biphase marked data. The Back Telemetry Controller (BTC) 1040 retrieves the biphase marked data from the RF receiver 1065, decodes it, and generates the BFSR and BCLKR for the DSP 1020. The Input/Output Ports 1045 provide expanded 10 functions to access the CPLD on-chip and off-chip devices. The Parallel Flash Memory (PFM) 1050 may be used to store executable code and the Serial Flash Memory (SFM) 1055 may provide Serial Port Interface (SPI) for data storage. The VIMC may be used to sample and monitor RF transmitter 1070 current and voltage in order to monitor the integrity status of the retinal stimulation system 1.

The following concepts are supported by the present application:

Concept 1. A visual prosthesis apparatus comprising:
a camera for capturing a video image;
a video processing unit associated with the camera, the video processing unit configured to convert the video image to stimulation patterns and comprising at least one indicator light to provide visual indication of operating status of the apparatus; and
a retinal stimulation system configured to stimulate neural tissue in a subject's eye based on the stimulation patterns.

Concept 2. The visual prosthesis apparatus of Concept 1 further comprising:
a fitting system connected with the video processing unit, the fitting system adapted to modify parameters in the video processing unit.

Concept 3. The visual prosthesis apparatus of Concept 1 or 2, wherein the retinal stimulation system comprises:
an electronics package;
an inductive coil electrically coupled to the electronics package;
an electrode array disposed on the subject's retina; and
a cable electrically coupling the electronics package and the electrode array.

Concept 4. The visual prosthesis apparatus of Concept 3, wherein the inductive coil comprises a receiver and transmitter antennae made from wound wire.

Concept 5. The visual prosthesis apparatus of Concept 3 or 4, wherein the electronics package comprises an Application Specific Integrated Circuit (ASIC) for processing the stimulation patterns and generating an output to stimulate the neural tissue in the subject's eye.

Concept 6. The visual prosthesis apparatus of Concept 3, 4 or 5 further comprising a second inductive coil, wherein the stimulation patterns and power are transmitted to the electronics package by the second inductive coil through the inductive coil of the retinal stimulation system.

Concept 7. The visual prosthesis apparatus of anyone of Concepts 1-6 further comprising an external inductive coil configured to transmit the stimulation patterns to the retinal stimulation system using radio-frequency (RF).

Concept 8. The visual prosthesis apparatus of Concept 7, wherein the external inductive coil comprises a receiver and transmitter antennae and a radio-frequency (RF) electronics card for communicating with the retinal stimulation system.

Concept 9. The visual prosthesis apparatus of Concept 7 or 8, wherein the external inductive coil and the camera are disposed on a pair of glasses.

Concept 10. The visual prosthesis apparatus of anyone of Concepts 1-9, wherein the retinal stimulation system is configured to transmit telemetry to the video processing unit, the telemetry identifying various operational conditions of the retinal stimulation system.

Concept 11. The visual prosthesis apparatus of anyone of Concepts 1-10, wherein the video processing unit comprises:
filters for processing and reducing resolution of the captured video image; and
a mapping function to adjust a stimulation intensity of the stimulation patterns.

Concept 12. The visual prosthesis apparatus of anyone of Concepts 1-11, wherein the video processing unit comprises:
a power button for turning the video processing unit on and off,
a settings button for controlling the video processing unit; and
zoom buttons for controlling the camera.

Concept 13. The visual prosthesis apparatus of Concepts 12, wherein at least two of the buttons of the video processing unit are of different shape to help identify a functionality of each button.

Concept 14. The visual prosthesis apparatus of Concepts 12 or 13, wherein at least one of the buttons of the video processing unit comprises at least one identification marking.

Concept 15. The visual prosthesis apparatus of anyone of Concepts 1-14, wherein the video processing unit comprises:
a first connector port for connecting the video processing unit to the camera; and a second connector port for connecting the video processing unit to a fitting system adapted to modify parameters in the video processing unit.

Concept 16. The visual prosthesis apparatus of anyone of Concepts 1-15, wherein the video processing unit is configured to shut off power to the retinal stimulation system in case of malfunction of the retinal stimulation system or the video processing unit.

Concept 17. The visual prosthesis apparatus of anyone of Concepts 1-16, wherein the at least one indicator light is configured to do at least one of a) through f):
 a) to indicate that the video processing unit is going through system start-up diagnostic testing by changing color and/or blinking;
 b) to indicate that the video processing unit is operating normally by changing color and/or blinking;
 c) to indicate that the retinal stimulation system has a problem that was detected at start-up diagnostic by changing color and/or blinking;
 d) to indicate that a signal from the camera is not being received by the video processing unit by changing color and/or blinking;
 e) to indicate that there is a loss of communication between the retinal stimulation system and the video processing unit while the visual prosthesis apparatus is operational by changing color and/or blinking; and
 f) to indicate if there is a problem with the retinal stimulation system by changing color and/or blinking.

Concept 18. A visual prosthesis apparatus comprising:
 a camera for capturing a video image;
 a video processing unit associated with the camera, the video processing unit configured to convert the video image to stimulation patterns and comprising a speaker to provide audible alerts to indicate various operational conditions of the apparatus; and
 a retinal stimulation system configured to stimulate neural tissue in a subject's eye based on the stimulation patterns.

Concept 19. The visual prosthesis apparatus of Concept 18, wherein the video processing unit is configured to do at least one of a) through k) with audio signals from the speaker:
 a) to indicate that the video processing unit is going through system start-up diagnostic testing;
 b) to indicate that the video processing unit is operating normally;
 c) to indicate that the retinal stimulation system has a problem that was detected at start-up diagnostic;
 d) to indicate that a signal from the camera is not being received by the video processing unit;
 e) to indicate that there is a loss of communication between the retinal stimulation system and the video processing unit while the visual prosthesis apparatus is operational;
 f) to indicate if there is a problem with the retinal stimulation system;
 g) to indicate that a button has been pressed;
 h) to indicate that the video processing unit is turned off;
 i) to indicate that the video processing unit is starting up;
 j) to indicate that an error has occurred and the video processing unit is about to shut down automatically; and
 k) to indicate a low battery voltage warning.

Concept 20. The visual prosthesis apparatus of Concept 19, wherein the audio signals from the speaker are beeps.

Concept 21. The visual prosthesis apparatus of Concept 20, wherein the audio signals from the speaker are prerecorded voice.

Concept 22. A video processing unit configured to convert a video image to stimulation patterns for stimulating neural tissue in a subject's eye and comprising at least one indicator light to provide visual indication of an operating status of at least the video processing unit.

Concept 23. The video processing unit of Concept 22, wherein the video processing unit comprises:
 filters for processing and reducing resolution of the video image; and
 a mapping function to adjust a stimulation intensity of the stimulation patterns.

Concept 24. The video processing unit of Concept 22 or 23, wherein the video processing unit comprises:
 a power button for turning the video processing unit on and off;
 a settings button for controlling the video processing unit; and
 zoom buttons for controlling a camera.

Concept 25. The video processing unit of Concept 24, wherein at least two of the buttons on the video processing unit are of different shape to help identify functionality of each button.

Concept 26. The video processing unit of Concept 24 or 25, wherein at least one of the buttons on the video processing unit comprises at least one identifying marking.

Concept 27. The video processing unit of anyone of Concepts 22-26, wherein the video processing unit comprises:
 a first connector port for connecting the video processing unit to a camera; and
 a second connector port for connecting the video processing unit to a fitting system adapted to modify parameters in the video processing unit.

Concept 28. The video processing unit of anyone of Concepts 22-27, wherein the video processing unit is configured to shut off power to the retinal stimulation system in case of malfunction of an implant or the video processing unit.

Concept 29. The video processing unit of anyone of Concepts 22-28, wherein the at least one indicator light is configured to do at least one of a) through f):
 a) to indicate that the video processing unit is going through system start-up diagnostic testing by changing color and/or blinking;
 b) to indicate that the video processing unit is operating normally by changing color and/or blinking;
 c) to indicate that an implant has a problem that was detected at start-up diagnostic by changing color and/or blinking;
 d) to indicate that a signal from a camera is not being received by the video processing unit by changing color and/or blinking;
 e) to indicate that there is a loss of communication between the implant and the video processing unit while the implant is operational by changing color and/or blinking; and
 f) to indicate if there is a problem with the implant by changing color and/or blinking.

Concept 30. A video processing unit configured to convert a video image to stimulation patterns for stimulating neural tissue in a subject's eye and comprises a speaker to provide audible alerts to indicate various operational conditions of at least the video processing unit.

Concept 31. The video processing unit of Concept 30, wherein the video processing unit is configured to do at least one of a) through k) with audio signals from the speaker:
 a) to indicate that the video processing unit is going through system start-up diagnostic testing;
 b) to indicate that the video processing unit is operating normally;
 c) to indicate that an implant has a problem that was detected at start-up diagnostic;
 d) to indicate that a signal from a camera is not being received by the video processing unit;
 e) to indicate that there is a loss of communication between the implant and the video processing unit while the visual prosthesis apparatus is operational;
 f) to indicate if there is a problem with the implant;
 g) to indicate that a button has been pressed;
 h) to indicate that the video processing unit is turned off;
 i) to indicate that the video processing unit is starting up;
 j) to indicate that an error has occurred and the video processing unit is about to shut down automatically; and
 k) to indicate a low battery voltage warning.

Concept 32. The video processing unit of Concept 31, wherein the audio signals from the speaker are beeps.

Concept 33. The video processing unit of Concept 32, wherein the audio signals from the speaker are prerecorded voice.

Concept 34. A method for providing artificial vision, the method comprising:
 capturing a video image;
 converting the video image to stimulation patterns;
 providing a visual indication of operating status of a system; and
 stimulating neural tissue in a subject's eye based on the stimulation patterns.

Concept 35. The method of Concept 34, wherein stimulation of the neural tissue is performed by a retinal stimulation system implanted in the subject and conversion of the video image is performed by a video processing unit.

Concept 36. The method of Concept 35 further comprising:
 providing an external inductive coil electrically connected with the video processing unit; and
 providing an internal inductive coil electrically connected with the retinal stimulation system, wherein both coils facilitate communication between the video processing unit and the retinal stimulation system.

Concept 37. The method of Concept 35 or 36, wherein converting the video image to stimulation patterns comprises:
 filtering the video image;
 reducing resolution of the video image; and
 adjusting stimulation intensity for the stimulation patterns.

Concept 38. A method for providing artificial vision, the method comprising:
 capturing a video image;
 converting the video image to stimulation patterns;
 providing an audio indication of operating status of a system; and
 stimulating neural tissue in a subject's eye based on the stimulation patterns.

Accordingly, what has been shown is an improved visual prosthesis, improved method of stimulating neural tissue and an improved method for controlling a visual prosthesis. While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. A visual prosthesis apparatus comprising:
 a camera for capturing a video image;
 a video processing unit, within a housing, including a connector on an outside surface of the housing, suitable for a user to detachably connect, disconnect and reconnect, the camera to the video processing unit the connector suitable to transmit the video image to the video processing unit;
 the video processing unit configured to convert the video image to stimulation patterns, to wirelessly transmit the stimulation patterns to a retinal stimulation system, wirelessly receive operational status signals from the retinal stimulation system, and comprising one or more indicator lights providing multiple indications to provide visual indication of operating status of the apparatus including safety and operational status signals received wirelessly from the retinal stimulation system, including an indication when video from the detachably connected camera is not received by the video processing system; and
 the retinal stimulation system configured to wirelessly receive the stimulation patterns and wirelessly transmit error signals to the video processing unit and to stimulate neural tissue in a subject's eye based on the stimulation patterns, and
 the one or more indicator lights being configured to be of different colors or emitting light with different blinking patterns, wherein said multiple indications are based on different combinations of colors or different blinking patterns.

2. The visual prosthesis apparatus of claim 1 further comprising:
 a fitting system connected with the video processing unit, the fitting system adapted to modify parameters in the video processing unit.

3. The visual prosthesis apparatus of claim 1, wherein the retinal stimulation system comprises:
 an electronics package;
 an inductive coil electrically coupled to the electronics package;
 an electrode array disposed on the subject's retina; and
 a cable electrically coupling the electronics package and the electrode array.

4. The visual prosthesis apparatus of claim 3, wherein the inductive coil comprises a receiver and transmitter antennae made from wound wire.

5. The visual prosthesis apparatus of claim 3, wherein the electronics package comprises an Application Specific Integrated Circuit (ASIC) for processing the stimulation patterns and generating an output to stimulate the neural tissue in the subject's eye.

6. The visual prosthesis apparatus of claim 3, further comprising a second inductive coil, wherein the stimulation patterns and power are transmitted to the electronics package by the second inductive coil through the inductive coil of the retinal stimulation system.

7. The visual prosthesis apparatus of claim 1, further comprising an external inductive coil configured to transmit the stimulation patterns to the retinal stimulation system using radio-frequency (RF).

8. The visual prosthesis apparatus of claim 7, wherein the external inductive coil comprises a receiver and transmitter antennae and a radio-frequency (RF) electronics card for communicating with the retinal stimulation system.

9. The visual prosthesis apparatus of claim 7, wherein the external inductive coil and the camera are disposed on a pair of glasses.

10. The visual prosthesis apparatus of claim 1, wherein the video processing unit comprises:
    filters for processing and reducing resolution of the captured video image; and
    a mapping function to adjust a stimulation intensity of the stimulation patterns.

11. The visual prosthesis apparatus of claim 1, wherein the video processing unit comprises:
    a power button for turning the video processing unit on and off;
    a settings button for controlling the video processing unit; and
    zoom buttons for controlling the camera.

12. The visual prosthesis apparatus of claim 11, wherein at least two of the buttons of the video processing unit are of different shape to help identify a functionality of each button.

13. The visual prosthesis apparatus of claim 11, wherein at least one of the buttons of the video processing unit comprises at least one identification marking.

14. The visual prosthesis apparatus of claim 1, wherein the video processing unit comprises:
    a first connector port for connecting the video processing unit to the camera; and
    a second connector port for connecting the video processing unit to a fitting system adapted to modify parameters in the video processing unit.

15. The visual prosthesis apparatus of claim 1, wherein the at least one indicator light is configured to do at least one of a) through f):
    a) to indicate that the video processing unit is going through system start-up diagnostic testing by changing color and/or blinking;
    b) to indicate that the video processing unit is operating normally by changing color and/or blinking;
    c) to indicate that the retinal stimulation system has a problem that was detected at start-up diagnostic by changing color and/or blinking;
    d) to indicate that a signal from the camera is not being received by the video processing unit by changing color and/or blinking;
    e) to indicate that there is a loss of communication between the retinal stimulation system and the video processing unit while the visual prosthesis apparatus is operational by changing color and/or blinking; and
    f) to indicate if there is a problem with the retinal stimulation system by changing color and/or blinking.

16. The visual prosthesis according to claim 1, wherein the multiple indications include flashing.

17. The visual prosthesis according to claim 16, wherein the multiple indications include flashing at varying rates.

18. The visual prosthesis according to claim 1, wherein the camera is supported on glasses and the video processing unit includes a connector port for connecting to glasses.

19. The visual prosthesis according to claim 1, wherein the video processing unit is a manually portable unit.

20. The visual prosthesis according to claim 1, wherein the video processing unit comprises a manually portable case and a plurality of buttons located on the case, the buttons being different from each other, to allow a user to identify different functionality associated with the buttons.

21. The visual prosthesis apparatus of claim 1, wherein the video processing unit is configured to shut off power to the retinal stimulation system in case of malfunction of the retinal stimulation system or the video processing unit.

22. A video processing unit configured to convert a video image to stimulation patterns for stimulating neural tissue in a subject's eye, wirelessly transmit the stimulation patterns to a stimulation system and wirelessly receive operational status signals from the stimulation system, the video processing unit being a structurally independent unit including a housing and a connector on an outside surface of the housing suitable for a user to detachably connect, disconnect and reconnect a camera, the connector suitable to transmit the video image to the video processing unit and comprising one or more indicator lights to provide visual indication of an operating status of the video processing unit and safety and operational status signals received wirelessly from the stimulation system, wherein the one or more indicator lights are configured to be of different colors or emitting light with different blinking patterns, wherein said multiple indications are based on different combinations of colors or different blinking patterns.

23. The video processing unit of claim 22, wherein the video processing unit comprises:
    filters for processing and reducing resolution of the video image; and
    a mapping function to adjust a stimulation intensity of the stimulation patterns.

24. The video processing unit of claim 22, wherein the video processing unit comprises:
    a power button for turning the video processing unit on and off;
    a settings button for controlling the video processing unit; and
    zoom buttons for controlling a camera.

25. The video processing unit of claim 24, wherein at least two of the buttons on the video processing unit are of different shape to help identify functionality of each button.

26. The video processing unit of claim 24, wherein at least one of the buttons on the video processing unit comprises at least one identifying marking.

27. The video processing unit of claim 22, wherein the video processing unit comprises:
    a first connector port for connecting the video processing unit to a camera; and
    a second connector port for connecting the video processing unit to a fitting system adapted to modify parameters in the video processing unit.

28. The video processing unit of claim 22, wherein the at least one indicator light is configured to do at least one of a) through f):
    a) to indicate that the video processing unit is going through system start-up diagnostic testing by changing color and/or blinking;
    b) to indicate that the video processing unit is operating normally by changing color and/or blinking;

c) to indicate that an implant has a problem that was detected at start-up diagnostic by changing color and/or blinking;
d) to indicate that a signal from a camera is not being received by the video processing unit by changing color and/or blinking;
e) to indicate that there is a loss of communication between the implant and the video processing unit while the implant is operational by changing color and/or blinking; and
f) to indicate if there is a problem with the implant by changing color and/or blinking.

29. The video processing unit of claim 22, wherein the video processing unit is configured to shut off power to the retinal stimulation system in case of malfunction of an implant or the video processing unit.

30. A method for providing artificial vision, the method comprising:
capturing a video image by using a camera;
detachably connecting a video processing unit having an housing to the camera through a connector on an outside surface of the housing on the video processing unit the connector suitable to transmit the video image to the video processing unit;
converting the video image to stimulation patterns by way of the video processing unit;
wirelessly transmitting the stimulation patterns to a stimulation system and wirelessly receiving operational status signals from the stimulation system;
providing a multiple visual indications of operating status of a system using one or more indicator lights including indications of operational status information and safety and operational status signals wirelessly transmitted from the stimulation system, and video from the detachably connected camera is not received by the video processing system; and
stimulating neural tissue in a subject's eye based on the stimulation patterns, wherein the one or more indicator lights are configured to be of different colors or emitting light with different blinking patterns, wherein said multiple indications are based on different combinations of colors or different blinking patterns.

31. The method of claim 30, wherein the retinal stimulation system is implanted in a subject.

32. The method of claim 31 further comprising:
providing an external inductive coil electrically connected with the video processing unit; and
providing an internal inductive coil electrically connected with the retinal stimulation system, wherein both coils facilitate communication between the video processing unit and the retinal stimulation system.

33. The method of claim 31, wherein converting the video image to stimulation patterns comprises:
filtering the video image;
reducing resolution of the video image; and
adjusting stimulation intensity for the stimulation patterns.

34. A visual prosthesis apparatus comprising:
a camera for capturing a video image;
a cable connected to the camera and a first detachable connector, the connector suitable to transmit the video image to the video processing unit;
a video processing unit including a housing and a second detachable connector on an outside surface of the housing, suitable for a user to connect to the first detachable connector, the video processing unit configured to convert the video image to stimulation patterns, wirelessly transmit the stimulation patterns and wirelessly receive operational status signals, and comprising one or more indicator lights providing multiple indications to provide visual indication of operating status of the apparatus including wirelessly received operational status signals; and
a retinal stimulation system configured to wirelessly receive the stimulation patterns and wirelessly transmit safety and operational status signals and to stimulate neural tissue in a subject's eye based on the stimulation patterns, and
the one or more indicator lights being configured to be of different colors or emitting light with different blinking patterns based on different operating conditions including wirelessly received the safety and optional status signals from the retinal stimulation system, wherein said multiple indications are based on different combinations of colors or different blinking patterns.

* * * * *